(12) United States Patent
Choi et al.

(10) Patent No.: US 8,346,031 B2
(45) Date of Patent: Jan. 1, 2013

(54) MICRO-RESONATOR SENSOR USING EVANESCENT WAVE OF TOTAL REFLECTION MIRROR

(75) Inventors: Young-Wan Choi, Seoul (KR); Doo Gun Kim, Seoul (KR)

(73) Assignee: Chung-Ang University Industry-Academy Cooperation Foundation, Seoul (KR)

( * ) Notice: Subject to any disclaimer, the term of this patent is extended or adjusted under 35 U.S.C. 154(b) by 253 days.

(21) Appl. No.: 12/993,777

(22) PCT Filed: Jun. 19, 2009

(86) PCT No.: PCT/KR2009/003301
§ 371 (c)(1),
(2), (4) Date: Nov. 19, 2010

(87) PCT Pub. No.: WO2010/005188
PCT Pub. Date: Jan. 14, 2010

(65) Prior Publication Data
US 2011/0075963 A1    Mar. 31, 2011

(30) Foreign Application Priority Data

Jul. 7, 2008    (KR) .................. 10-2008-0065487

(51) Int. Cl.
*G02B 6/00* (2006.01)
*G01J 3/44* (2006.01)
(52) U.S. Cl. ............... 385/12; 385/2; 385/15; 356/300; 356/301; 356/302; 356/303; 356/432; 356/436
(58) Field of Classification Search ............. 385/2, 12, 385/15; 356/300–303, 432, 436
See application file for complete search history.

(56) References Cited

U.S. PATENT DOCUMENTS

| 7,336,859 | B2 | 2/2008 | Sanders |
| 7,435,944 | B2* | 10/2008 | Ja et al. ............ 250/227.14 |
| 2002/0097401 | A1* | 7/2002 | Maleki et al. ............ 356/436 |
| 2004/0023396 | A1* | 2/2004 | Boyd et al. ............ 435/872 |
| 2005/0210989 | A1* | 9/2005 | Ja et al. ............ 73/705 |
| 2006/0170931 | A1* | 8/2006 | Guo et al. ............ 356/480 |
| 2007/0109550 | A1* | 5/2007 | Ja et al. ............ 356/480 |

(Continued)

FOREIGN PATENT DOCUMENTS
JP    11-094859    4/1999

(Continued)

*Primary Examiner* — Brian Healy
*Assistant Examiner* — Guy Anderson
(74) *Attorney, Agent, or Firm* — Occhiuti Rohlicek & Tsao LLP

(57) ABSTRACT

A micro-resonator sensor uses an evanescent wave of a total reflection mirror. The sensor includes an input waveguide for guiding inspection light incidented on one end section to the other section. A total reflection mirror is disposed at the other section of the input waveguide such that an incident angle made with the input waveguide is larger than a total reflection threshold angle at which the inspection light is totally reflected, and includes a receptor provided on the other side from the side on which the inspection light is incidented and combined with a measurement-subject material. An output waveguide is disposed at a certain output angle relative to the total reflection mirror for outputting a reflection light whose intensity changes according to the measurement-subject material due to an interaction between the evanescent wave generated by the inspection light incidented to the total reflection mirror and the measurement-subject material.

14 Claims, 6 Drawing Sheets

U.S. PATENT DOCUMENTS

| | | | |
|---|---|---|---|
| 2007/0152142 A1* | 7/2007 | Ja et al. | 250/227.14 |
| 2007/0258677 A1* | 11/2007 | Chigrinov et al. | 385/15 |
| 2008/0101744 A1* | 5/2008 | Keyser et al. | 385/12 |
| 2008/0266573 A1* | 10/2008 | Choi et al. | 356/481 |

FOREIGN PATENT DOCUMENTS

| | | |
|---|---|---|
| JP | 2004-077411 | 3/2004 |
| KR | 10-0839967 | 6/2008 |

* cited by examiner

MICRO-RESONATOR SENSOR USING EVANESCENT WAVE OF TOTAL REFLECTION MIRROR

CROSS-REFERENCE TO RELATED APPLICATIONS

This application is the National Stage of International Application No. PCT/KR2009/003301 filed Jun. 19, 2009, which claims the priority of Korean Application No. 10-2008-0065487, filed on Jul. 7, 2008. The contents of both applications are hereby incorporated by reference in their entirety.

TECHNICAL FIELD

The present invention is related to a micro-resonator sensor and, more particularly, to a micro-resonator sensor for detecting the characteristics of a measurement-subject material (i.e., subject (substance) to be measured) by using interaction between an evanescent wave of a total reflection mirror and the measurement-subject material.

BACKGROUND ART

In general, a micro-resonator sensor detects the characteristics of a measurement-subject material by detecting the intensity of light at an output terminal of a waveguide which corresponds to a change in an effective refractive index of a ring resonator, which is installed separately from the waveguide, when light proceeding through the waveguide including an input terminal and the output terminal is coupled to the ring resonator.

FIG. 1 illustrates the related art micro-ring resonator sensor.

With reference to FIG. 1, the related art micro-ring resonator sensor includes a main waveguide 110 and a ring resonator 120. The main waveguide 110 is formed as an optical fiber or an optical waveguide (or light waveguide), and both ends of the main waveguide 110 serve as an input terminal to which optical signal is inputted and an output terminal from which the optical signal is outputted, respectively. The ring resonator 120 is an annular optical fiber or an optical waveguide with a certain radius (R), including an opening 122 whose surface is interface-treated so that light proceeding through the optical fiber or the optical waveguide constituting the ring resonator 120 can effectively react to a liquid or gas, a measurement-subject material. Such opening 122 is formed at an upper surface or a side surface of the optical fiber or optical waveguide constituting the ring resonator 120. A optical transmission mode that can be accommodated by the micro-ring resonator sensor is determined depending on where the opening 122 is formed. Thus, if the opening 122 is formed at both on the upper surface and on the side surface of the ring resonator 120, the micro-ring resonator sensor can receive both optical signals of a TM mode and a TE mode. The main waveguide 110 and the ring resonator 120 are separately disposed on a single dielectric substrate to constitute the ring resonator sensor.

In the related art micro-ring resonator sensor as shown in FIG. 1, an optical signal inputted through the input terminal of the main waveguide 110 proceeds along the main waveguide 110 and is then coupled to the ring resonator 120 disposed to be separated from the main waveguide 110 according to resonance conditions of the ring resonator 120. The light incidented to the ring resonator 120 is reacted to a liquid or gaseous bio-material, a measurement-subject material, on the interface-treated surface of the opening 122 formed at the ring resonator 120, and accordingly, an effective refractive index of the ring resonator 120 changes. The change in the effective refractive index of the ring resonator 120 triggers a change in conditions for optical coupling from the main waveguide 110 to the ring resonator 120. Namely, the effective refractive index of the ring resonator 120 changes according to the density of the material reacting on the upper surface and on the side surface of the ring resonator 120, and accordingly, the amount of outputted light through the output terminal of the main waveguide 110 varies, thus detecting the characteristics of the material. Configuration of a biotransducer by introducing a biological element to the opening 122 of the ring resonator 120 makes it possible to fabricate a bio-sensor using the ring resonator.

If the resonance conditions are met, optical coupling from the main waveguide 110 to the ring resonator 120 occurs, and if threshold coupling conditions are met, the optical signal is not outputted to the output terminal of the main waveguide 110. The intensity of the optical signal coupled from the main waveguide 110 to the ring resonator 120 is maximized at a point of time when the threshold coupling conditions are met.

FIG. 2 is a graph of characteristic curved line of an outputted light versus wavelengths of incident light according to the resonance conditions of the ring resonator 120. With reference to FIG. 2, when a threshold coupling occurs under the resonance conditions of the ring resonator 120, there is no output from the output terminal of the main waveguide 110 at a minimum wavelength, and the minimum wavelength is shifted according to interaction between bio-molecules. Namely, the wavelength of a optical signal at which no output is generated from the output terminal of the main waveguide 110 varies according to a variation of the effective refractive index of the ring resonator 120 by the measurement-subject material brought into contact with the opening 122 of the ring resonator 120. In FIG. 2, it is noted that each time the effective refractive index of the ring resonator 120 increases by $1 \times 10^{-4}$, the minimum wavelength at which there is no output from the output terminal of the main waveguide 110 is increased uniformly. Thus, the ring resonator sensor can detect the characteristic of the measurement-subject material by measuring a response signal with respect to the strength (intensity) and wavelength of the optical signal output through the output terminal of the main waveguide 110.

The output of the ring resonator sensor is very sensitive to a change in the dielectric constant of a medium occurring when the medium comes in contact with the opening 122 formed at the ring resonator 120. Namely, as the medium flows (moves) through the opening 122 of the ring resonance sensor, the dielectric constant of the medium changes, and accordingly, the effective refractive index of the ring resonator 120 is also changed. Such change in the effective refractive index of the ring resonator 120 causes the resonance conditions to be changed, making the output wavelength shifted. Thus, the ring resonator sensor detects the characteristics of the measurement-subject material by detecting the density of the measurement-subject material by the effective refractive index of the ring resonator 120 calculated based on the strength and the phase of the optical signal measured at the output terminal of the main waveguide 110.

However, the related art ring resonator sensor is advantageous in that the characteristics of the measurement-subject material can be measured through the simple structure, but it has a limitation in terms of reducing the size of the sensor. Namely, for the related art ring resonator sensor including the resonator with an optical waveguide in the circular loop form, in order to reduce the radius of the ring resonator without an excessive radiation loss, the periphery of the optical waveguide constituting the ring resonator needs to be deeply etched. Deeply etching the periphery of the optical waveguide can enhance a side optical confinement effect of the optical waveguide, but increases a optical propagation loss due to a sidewall roughness. In addition, if the optical waveguide itself constituting the ring resonator is made of an intrinsic material, etching through the intrinsic material causes a problem due to an excessive surface recombination. In addition, such ring resonator increases a radiation loss, resulting in an obstacle factor to reduction in size of the ring resonance sensor.

DISCLOSURE OF INVENTION

Technical Problem

Therefore, an object of the present invention is to provide a micro-resonance sensor using an evanescent wave of a total reflection mirror integrated as an on-chip so as to be used any time and anywhere and minimizing a radiation loss according to a reduction in size of the sensor.

Technical Solution

To achieve the above object, in one aspect, there is provided a micro-resonator sensor using an evanescent wave of a total reflection mirror, including: an input waveguide guiding inspection light incidented on one end section thereof to the other section; a total reflection mirror disposed at the other section of the input waveguide such that an incident angle made with the input waveguide is larger than a total reflection threshold angle at which the inspection light is totally reflected, and including a receptor provided on the other side from the side on which the inspection light is incidented and combined with a measurement-subject material; and an output waveguide disposed at a certain output angle relative to the total reflection mirror and outputting a reflection light whose intensity changes according to the measurement-subject material due to an interaction between the evanescent wave generated by the inspection light incidented to the total reflection mirror and the measurement-subject material.

To achieve the above object, in another aspect, there is also provided a micro-resonance sensor using an evanescent wave of a total reflection mirror, including: a main waveguide comprising an input hole to which a optical signal is incidented and a output hole from which the optical signal is outputted and having a optical coupling region at which a portion of the optical signal incidented through the input hole is branched; a resonant waveguide comprising a optical coupling waveguide having a optical coupling region optically coupled with the optical coupling region of the main waveguide to receive the branch optical signal branched from the main waveguide, and a plurality of circumferential waveguides, the optical coupling waveguide and the circumferential waveguides of the resonance waveguide being disposed in a polygonal shape; and a plurality of optical path changing units disposed at vertex regions to which the optical coupling waveguide and the circumferential waveguides constituting the resonant waveguide are connected, and reflecting at least a portion of the branch optical signal inputted to the resonant waveguide so that the reflected optical signal can turn around within the resonant waveguide, wherein at least one of the optical path changing units disposed at the vertex regions to which the circumferential waveguides are connected is a total reflection mirror comprising a receptor provided on the other side from the side on which the branch optical signal is incidented and combined with a measurement-target material, the one circumferential waveguide, which makes the branch optical signal incident to the total reflection mirror, is disposed such that an incident angle relative to the total reflection mirror is larger than a total reflection threshold angle to make the branch optical signal incident on the total reflection mirror totally-reflected, the other circumferential waveguide, from which the branch optical signal totally reflected by the total reflection mirror is outputted, is disposed to make a certain output angle relative to the total reflection mirror, and resonance conditions of the resonant waveguide vary depending on the measurement-subject material.

Advantageous Effects

In the micro-resonator sensor according to the present invention, a polygonal resonator including total reflection mirrors is configured by using a general optical waveguide. Thus, the micro-resonator sensor can be fabricated with an ultra-compact size without an excessive radiation loss. In addition, because the total reflection mirrors are disposed near the vertexes of the polygonal resonator such that an evanescent wave can increase, the high-sensitivity micro-resonator sensor can be fabricated. Also, because all the elements are integrated on a single wafer, the micro-resonator sensor can be fabricated as an on-chip, whereby an ultra-compact optical sensor module applicable to mobile terminals can be manufactured.

MODE FOR THE INVENTION

A micro-resonator sensor using an evanescent wave of a total reflection mirror according to exemplary embodiments of the present invention will now be described in detail with reference to the accompanying drawings.

Figure 1:
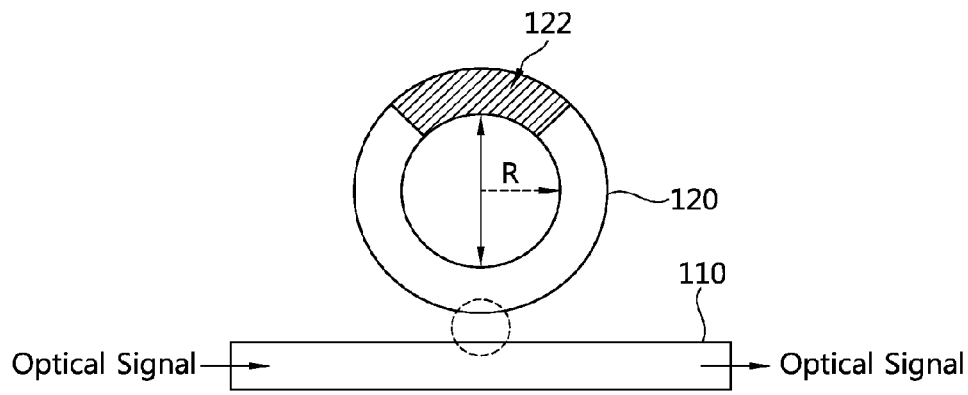
FIG. 1 illustrates the related art micro-ring resonator sensor.
Figure 2:
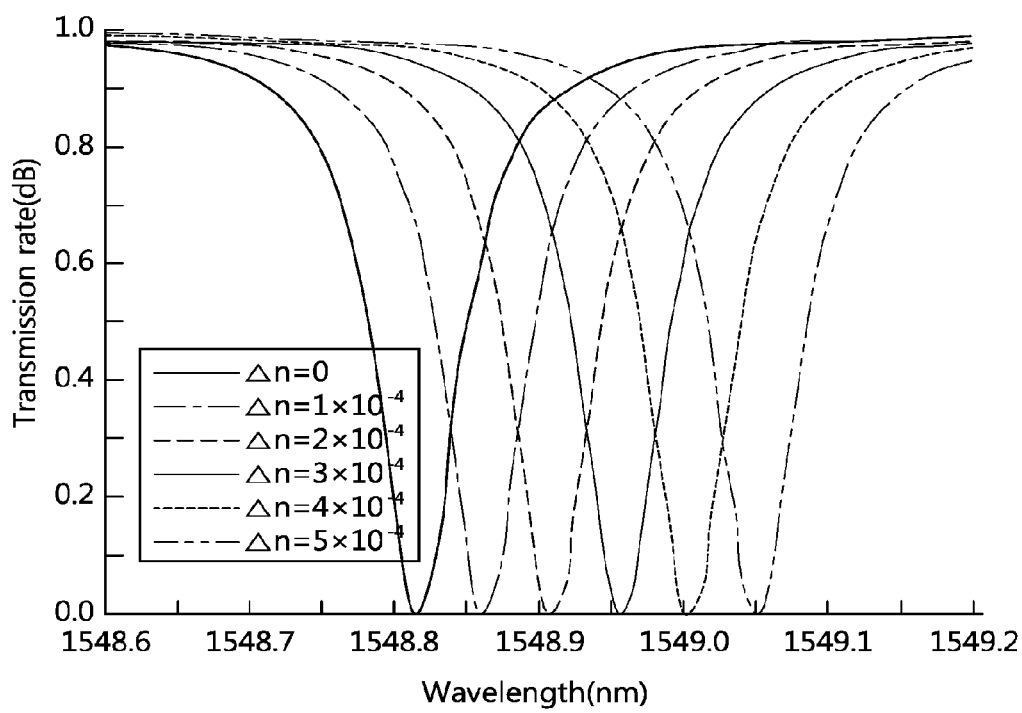
FIG. 2 is a graph of characteristic curved lines of outputted light over resonance conditions of a ring resonator of the related art micro-ring resonator sensor.
Figure 3:
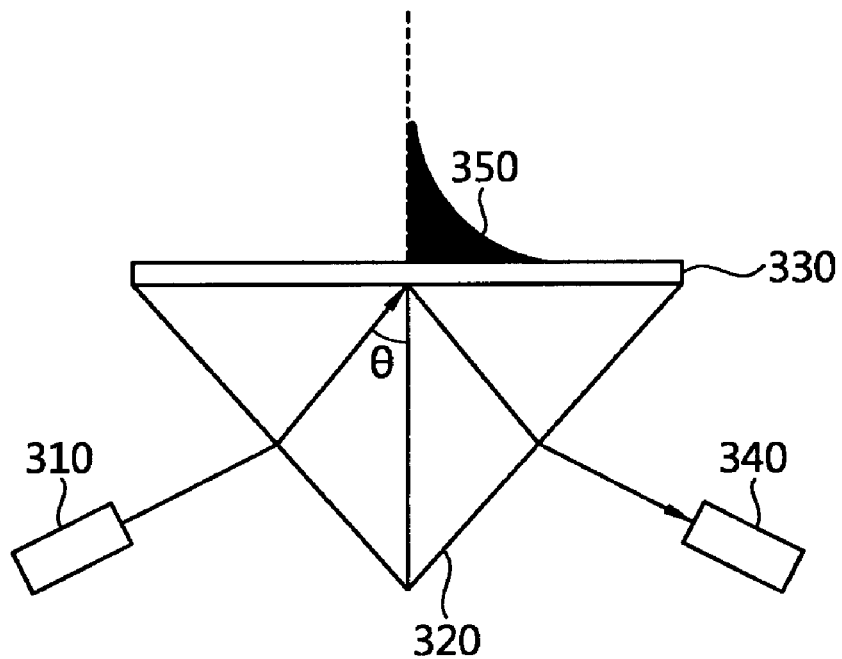
FIG. 3 and FIG. 4 are views for explaining the principle of an evanescent wave formed on a total reflection mirror.
Figure 4:
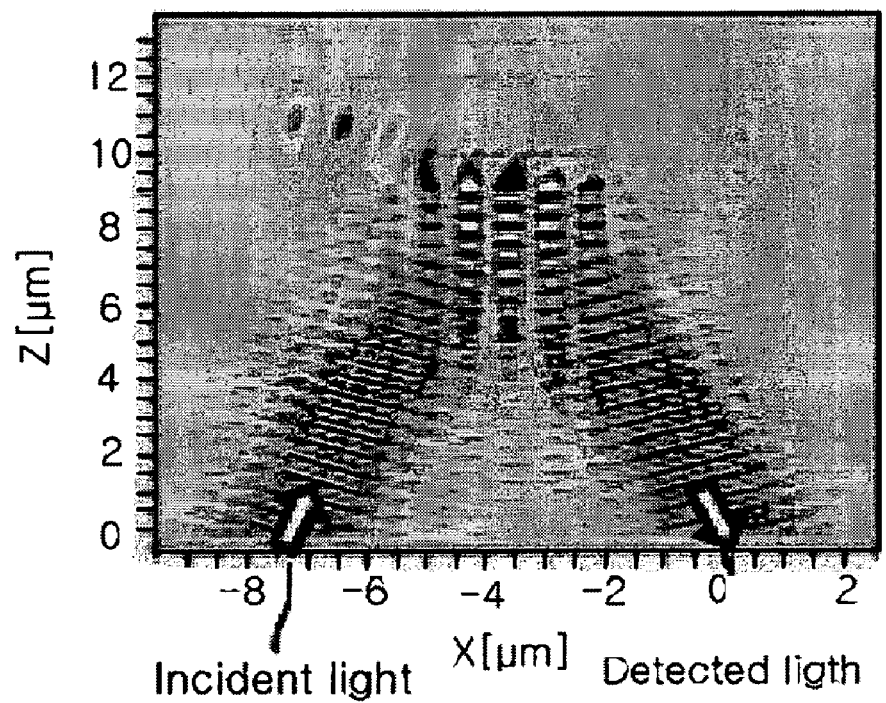

FIG. 3 and FIG. 4 are views for explaining the principle of an evanescent wave formed on a total reflection mirror.

As shown in FIG. 3, when monochromatic light such as laser emitted from a light source unit 310 is incidented to a medium with high refractive index such as a prism 320, the light incidented to the prism 320 is reflected from a total reflection mirror 330 positioned at the bottom surface of the prism 320 to reach a detecting unit 340 positioned at the opposite side of the light source unit 310. When the incident light is incidented to the total reflection mirror 330, an evanescent wave 350 is generated. The evanescent wave 350 increases as an incident angle (θ) of the incident light becomes smaller, so in order to increase the sensitivity of the micro-resonator sensor using the evanescent wave, the incident angle (θ) needs to be small.

In this respect, however, if the incident angle (θ) of the incident light is the same as a total reflection threshold angle, the incident light would entirely proceed along the interface of the total reflection mirror 330, making it impossible for the detecting unit 340 to detect light. Meanwhile, if the incident angle (θ) of the incident light is smaller than the total reflection threshold angle, a transmission light is generated, making it impossible for the detecting unit 340 to obtain a reliable measurement value. Thus, in order to detect a measurement-subject material through the micro-resonator sensor using an evanescent wave, preferably, the incident angle (θ) of the incident light is larger than the total reflection threshold angle but as close as possible to the total reflection threshold angle.

In order to check the evanescent wave 350 formed on the total reflection mirror 330, proceeding of light is calculated according to a finite-difference time-domain method as shown in FIG. 4. A refractive index of the total reflection mirror 330 used for the calculation was 3.291, and a total reflection threshold angle was about 17°. It is noted in FIG. 4 that the evanescent wave expands when the incident angle (θ) of the incident light is 20°.

Figure 5:
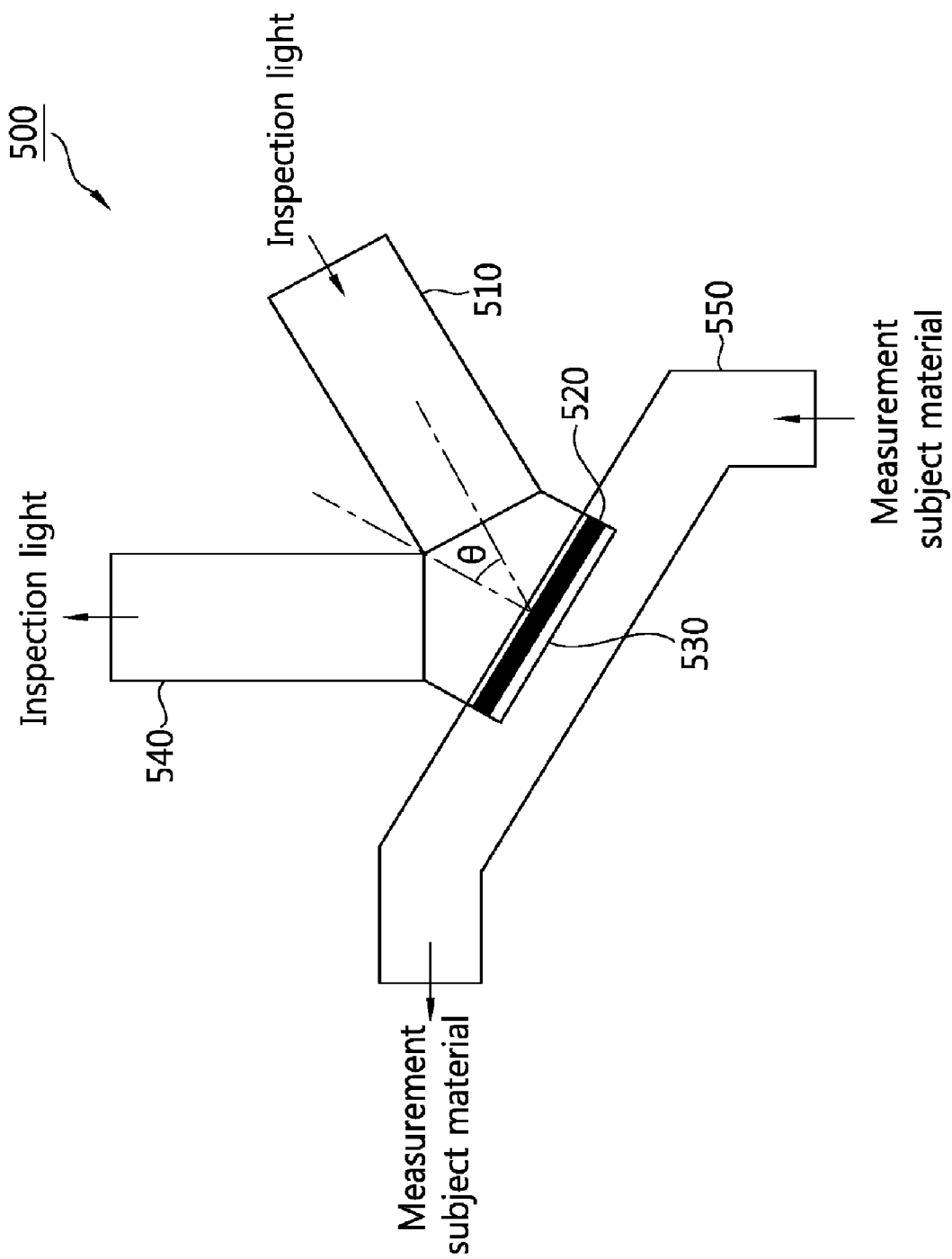
FIG. 5 illustrates the configuration of a micro-resonance sensor according to a first embodiment of the present invention.

FIG. 5 illustrates the configuration of a micro-resonance sensor according to a first embodiment of the present invention.

With reference to FIG. 5, the micro-resonator sensor 500 according to the first embodiment of the present invention includes an input waveguide 510, a total reflection mirror 520, an output waveguide 540, and a flow path unit 550.

Inspection light emitted from a light source unit is incidented through one end section of the input waveguide 510. As the light source unit, a general wavelength variable light source may be used. The input waveguide 510 guides the incident inspection light to the other section thereof.

The total reflection mirror 520 is connected with the input waveguide 510 at a certain angle (θ) based on a normal perpendicular to a front surface of the total reflection mirror 520 such that an inspection light can be totally reflected. The angle between the input waveguide 510 and the normal is defined as an incident angle (θ) of the inspection light. The incident angle (θ) is set to be larger than a total reflection threshold value and set such that energy in the form of evanescent wave transferred to the opposite side of the total reflection mirror 520 is stronger than a pre-set value. Preferably, the incident angle (θ) is set to be closest to the total reflection threshold angle. When the incident angle (θ) is set to be so close to the total reflection threshold value, the evanescent wave expands as mentioned above. The expansion of the evanescent wave leads to a clear change in the intensity of light detected according to a measurement-subject material. Thus, the incident angle (θ) needs to set such that the evanescent wave becomes larger, to make the micro-resonator sensor have good sensitivity.

A receptor 530 to be combined with the measurement-subject material is fixed to a rear surface of the total reflection mirror 520.

One end section of the output waveguide 540 is connected at the same angle with the incident angle (θ) based on the normal perpendicular to the front surface of the total reflection mirror 520, and guides the inspection light reflected by the total reflection mirror 520 so as to be outputted. The other section of the output waveguide 540 is connected to a detecting unit (not shown).

The flow path unit 550 provides a path along which a gaseous or liquid measurement-subject material flows. The flow path unit 550 is formed in a tubular shape. The measurement-subject material is inputted to one end and outputted from the other end of the flow path unit 550. An opening is formed at a middle section of the flow path unit 550, in which the receptor 530 fixed to the total reflection mirror 520 is insertedly positioned and hermetically closed so as to be maintained within the flow path unit 550. With such configuration, the measurement-subject material introduced into the flow path unit 550 reacts to the receptor 530 fixed to the total reflection mirror 520.

The detecting unit (not shown) detects the intensity of outputted light through the output waveguide 540. The detecting unit analyzes the intensity of the outputted light through the output waveguide 540 to deduce the characteristics (e.g., density) of the measurement-subject material.

If the refractive index of the measurement-subject material changes, the threshold angle of the total reflection changes. In more detail, as the refractive index of the measurement-subject material increases, the threshold angle of the total reflection increases. With the incident angle (θ) fixed, if the threshold angle of the total reflection increases, the incident angle (θ) becomes close to the threshold angle of the total reflection, expanding the evanescent wave. The evanescent wave interacts with the measurement-subject material, causing an energy loss. Thus, if the evanescent wave expands, it would actively interact with the measurement-subject material, increasing the energy loss in the form of evanescent wave. Thus, as the reflective index of the measurement-subject material increases, the intensity of light measured by the detecting unit decreases. By analyzing this, the refractive index of the measurement-subject material can be deduced, from which the characteristics of the measurement-subject material can be detected.

Namely, in the micro-resonator sensor 500 according to the first embodiment of the present invention, the inspection light with a particular wavelength is inputted to the input waveguide 510 through the light source unit, and the inspecting unit detects the intensity of the light corresponding to the particular wavelength to detect the characteristics of the measurement-subject material.

Figure 6:
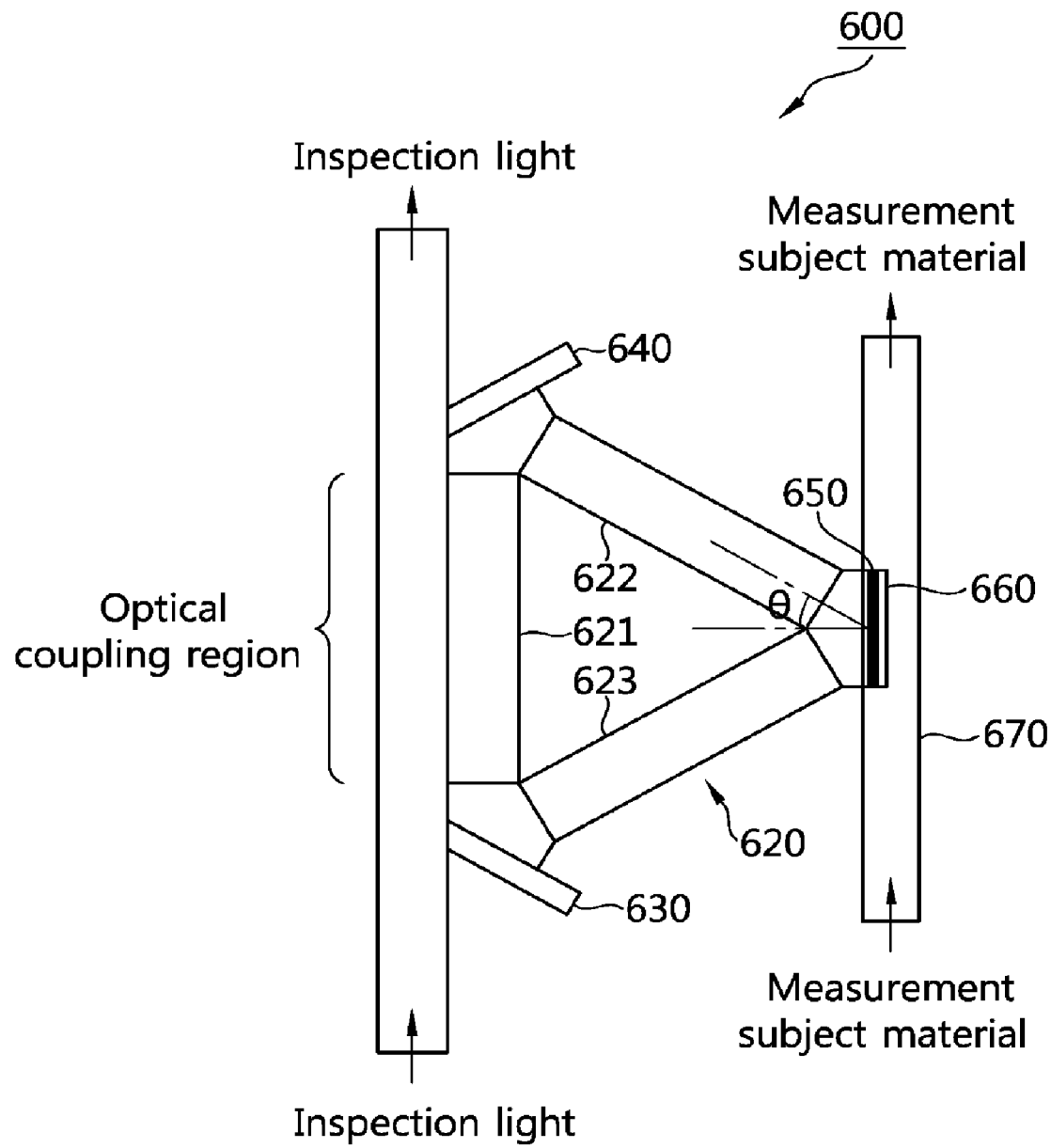
FIG. 6 illustrates the configuration of a micro-resonance sensor according to a second embodiment of the present invention.

FIG. 6 illustrates the configuration of a micro-resonance sensor according to a second embodiment of the present invention.

With reference to FIG. 6, a micro-resonator sensor 600 according to the second embodiment of the present invention includes a main waveguide 610, a resonant waveguide 620, and total reflection mirrors 630, 640, and 650.

The main waveguide 610 includes an input hole (i.e., input section) to which optical signal is incidented and an output hole (i.e., output section) from which the optical signal is outputted. The main waveguide 610 includes a optical coupling region at which the light is inputted through the input hole is coupled to the resonant waveguide 620. Inspection light emitted from a light source unit is incidented to the input hole of the main wave guide 610. As the light source unit, a general wavelength variable light source may be used.

The resonant waveguide 620 includes a optical coupling waveguide 621 having a optical coupling region optically coupled with the optical coupling region of the main waveguide 610 and receiving a branch optical signal to be coupled to the resonant waveguide 620 among the light which has been inputted through the input hole of the main waveguide 610, and two circumferential waveguides 622 and 623. The optical coupling waveguide 621 and the circumferential waveguides 622 and 623 are disposed in a triangular shape. The optical coupling waveguide 621 is disposed to be parallel to the main waveguide 610.

The optical coupling regions formed at the main waveguide 610 and the resonant waveguide 620 are formed as a optical coupling element for coupling the optical signal incidented to the main waveguide 610 to the resonant waveguide 620 or coupling optical signal turning around (i.e., rotating) within the resonant waveguide 620 to the main waveguide 610. The optical coupling element used therefor is a vertical coupler, a directional coupler, or a multi-mode coupler. The vertical coupler, the directional coupler, and the multi-mode coupler are known elements, so their detailed description will be omitted.

The total reflection mirrors 630, 640, and 650 are disposed at vertex regions where the optical coupling waveguide 621 and the circumferential waveguides 622 and 623 constituting the three sides of the triangular resonant waveguide 620 are connected to each other, and reflect the branch optical signal such that the branch optical signal can turn around within the resonant waveguide 620. In FIG. 6, the total reflection mirrors 630, 640, and 650 are illustrated to reflect the branch optical signal so as to turn around within the resonant waveguide 620, but the present invention is not meant to be limited thereto and any means for changing a optical path of at least a portion of the branch optical signal to make the portion of the branch optical signal turn around within the resonant waveguide 620 may be disposed at the vertex regions of the resonant waveguide 620.

Meanwhile, the total reflection mirror 650 disposed at one vertex region, to which the circumferential waveguides 622 and 623 are connected, is disposed at a certain angle ($\theta$) relative to the circumferential waveguide 622 making the branch optical signal incident based on a normal perpendicular to the front surface of the total reflection mirror 650, so that the incident branch optical signal can be totally reflected. The angle between the circumferential waveguide 622 making the branch optical signal incident and the normal of the total reflection mirror 650 disposed at the vertex region to which the circumferential waveguides 622 and 623 is defined as an incident angle ($\theta$). As discussed above, the incident angle ($\theta$) is set to be larger than the total reflection threshold angle and set such that energy in the form of evanescent wave transferred to the opposite side of the total reflection mirror 650 is stronger than a pre-set value. Preferably, the incident angle ($\theta$) is set to be closest to the total reflection threshold angle. With such incident angle ($\theta$) set, a change degree of an effective refractive index of the resonant waveguide 620 increases according to a refractive index of a measurement-subject material. The increase in the change degree of the effective refractive index of the resonant waveguide 620 makes a change degree of the resonance conditions of the resonant waveguide 620 increases, according to which the characteristics of the measurement-subject material can be clearly detected.

A receptor 660 coupled with the measurement-subject material is fixed to a rear surface of the total reflection mirror 650 disposed at the vertex region to which the circumferential waveguides 622 and 623 are connected. The circumferential waveguide 623 to which the branch optical signal totally reflected by the total reflection mirror 650 disposed at the vertex region, to which the circumferential waveguides 622 and 623 are connected, is disposed at the same angle as the incident angle ($\theta$) based on the normal perpendicular to the front surface of the total reflection mirror 650.

The main waveguide 610 and the optical coupling waveguide 621 constituting the resonant waveguide 620 may be integrally formed. The total reflection mirrors are disposed at both end sections of a optical coupling region. One of the total reflection mirrors is disposed at an end section of the optical coupling region adjacent to the output hole of the main waveguide 610 and branches a optical signal incidented through the input hole of the main waveguide 610 to the output hole of the main waveguide 610 and the resonant waveguide 620. Another one of the total reflection mirrors is disposed at an end section of the optical coupling region adjacent to the input hole of the main waveguide 601 and branches a branch optical signal which has turned around within the resonant waveguide 620 to the main waveguide 610 and the resonant waveguide 620.

A flow path unit 670 provides a flow path allowing gaseous or liquid measurement-subject material flow therethrough. The flow path unit 670 is formed in a tubular shape. The measurement-subject material is inputted to one end of the flow path unit 670 and outputted from another end of the flow path unit 670. An opening is formed at a middle section of the flow path unit 670, in which the receptor 660 fixed to the total reflection mirror 650 disposed at the vertex region to which the circumferential waveguides 622 and 623 are connected is insertedly positioned and hermetically closed so as to be maintained within the flow path unit 670. With such configuration, the measurement-subject material introduced into the flow path unit 670 reacts to the receptor 660 fixed to the total reflection mirror 650.

With the incident angle ($\theta$) fixed, when the refractive index of the measurement-subject material combined with the receptor 660 changes, an effective refractive index of the resonant waveguide 620 changes. As the effective refractive index of the resonant waveguide 620 changes, the resonance conditions of the resonant waveguide 620 changes. A detecting unit (not shown) positioned at the output hole of the main waveguide 610 measures the intensity of light corresponding to a particular wavelength, and in this case, if the resonance conditions of the resonant waveguide 620 change, the intensity of light measured by the detecting unit also changes. Namely, the intensity of light corresponding to the particular wavelength changes according to a measurement-subject material, based on which the refractive index of the measurement-subject material can be deduced, from which the characteristics (i.e., density) of the measurement-subject material can be detected.

The configuration of the resonant waveguide 620 including the optical coupling waveguide 621 and two circumferential waveguides 622 and 623 disposed in the triangular shape as shown in FIG. 6 have been described, but the present invention is not meant to be limited thereto and the resonant waveguide 620 may include the optical coupling waveguide 621 and three or more circumferential waveguides disposed in a polygonal shape and performed in a similar manner.

Figure 7:
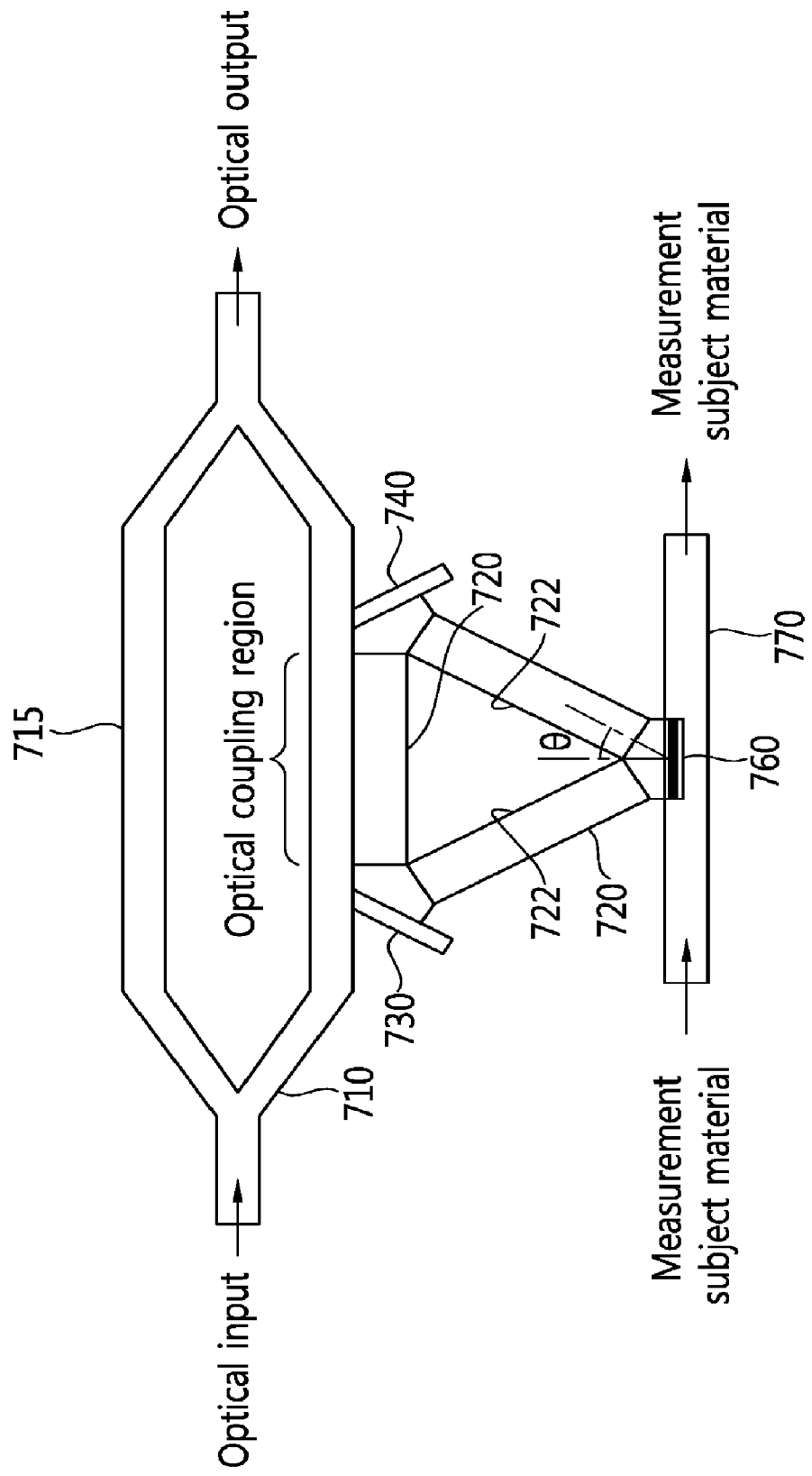
FIG. 7 illustrates the configuration of a micro-resonance sensor according to a third embodiment of the present invention.

FIG. 7 illustrates the configuration of a micro-resonance sensor according to a third embodiment of the present invention. The micro-resonance sensor 700 according to the third embodiment of the present invention as shown in FIG. 7 has a structure that the micro-resonance sensor 600 according to the second embodiment as shown in FIG. 6 is combined with a Mach-Zehnder electrooptic modulator.

With reference to FIG. 7, in the micro-resonance sensor 700 according to the third embodiment of the present invention, a resonant waveguide 720 having vertexes at which total reflection mirrors 730, 740, and 750 are disposed is combined with one optical waveguide 710 among two optical waveguides 710 and 715 constituting a Mach-Zehnder electrooptic modulator. When a optical signal is incidented through an input hole of the Mach-Zehnder electrooptic modulator formed on an electrooptic material, it passes through the two different optical waveguides 710 and 715, being combined again into a single optical signal, which is then outputted to an output hole of the Mach-Zehnder electrooptic modulator. At this time, If voltage is applied to one of the optical waveguides (e.g., 715), the refractive index of the optical waveguide 715 changes to cause a phase change of the signal, making the signal constructively or destructively interfere with the optical signal of another optical waveguide 710, thus enabling modulation of the input signal.

The optical signal incidented through one optical waveguide 710 of the Mach-Zehnder electrooptic modulator is coupled to a optical coupling waveguide 721 constituting the resonant waveguide 720 disposed to be parallel to the optical waveguide 710, which is then inputted to the resonant waveguide 720. The optical signal input to the resonant waveguide 720 is reflected by the total reflection mirrors 730, 740, and 750 disposed at the vertexes of the resonant waveguide 720 to turn around within the resonant waveguide 720 through the optical coupling waveguide 721 and two circumferential waveguides 722 and 723. In the micro-resonance sensor 700 according to the third embodiment of the present invention as shown in FIG. 7, the resonant waveguide 720, the total reflection mirrors 730, 740, and 750, and a flow path unit 770 correspond to the resonant waveguide 620, the total reflection mirrors 630, 640, and 650 and the flow path 670 of the micro-resonance sensor 600 according to the second embodiment of the present invention as shown in FIG. 6.

Namely, similarly as described above with reference to FIG. 6, if the refractive index of a measurement-subject material changes, the effective refractive index of the resonant waveguide 720 changes, and accordingly, the resonance conditions of the resonant waveguide 720 change. Also, optical coupling conditions between the resonant waveguide 720 and the optical waveguide 710 of the Mach-Zehnder electrooptic modulator combined to the resonant waveguide 720 vary according to the change in the resonance conditions. Accordingly, the optical signal outputted from the optical waveguide 710 of the Mach-Zehnder electrooptic modulator optically combined with the resonant waveguide 720 changes according to the characteristics of the measurement-subject material combined to a receptor 760. A optical signal outputted from one optical waveguide 710 of the Mach-Zehnder electrooptic modulator optically combined with the resonant waveguide 720 and a optical signal outputted from another optical waveguide 715 constructively or destructively interfere with each other to change the intensity of outputted light through the output hole of the Mach-Zehnder electrooptic modulator. A detecting unit (not shown) detects it and calculates a variation of the resonance conditions of the resonant waveguide 720 to thus detect the characteristics (e.g., density) of the measurement-subject material.

Figure 8:
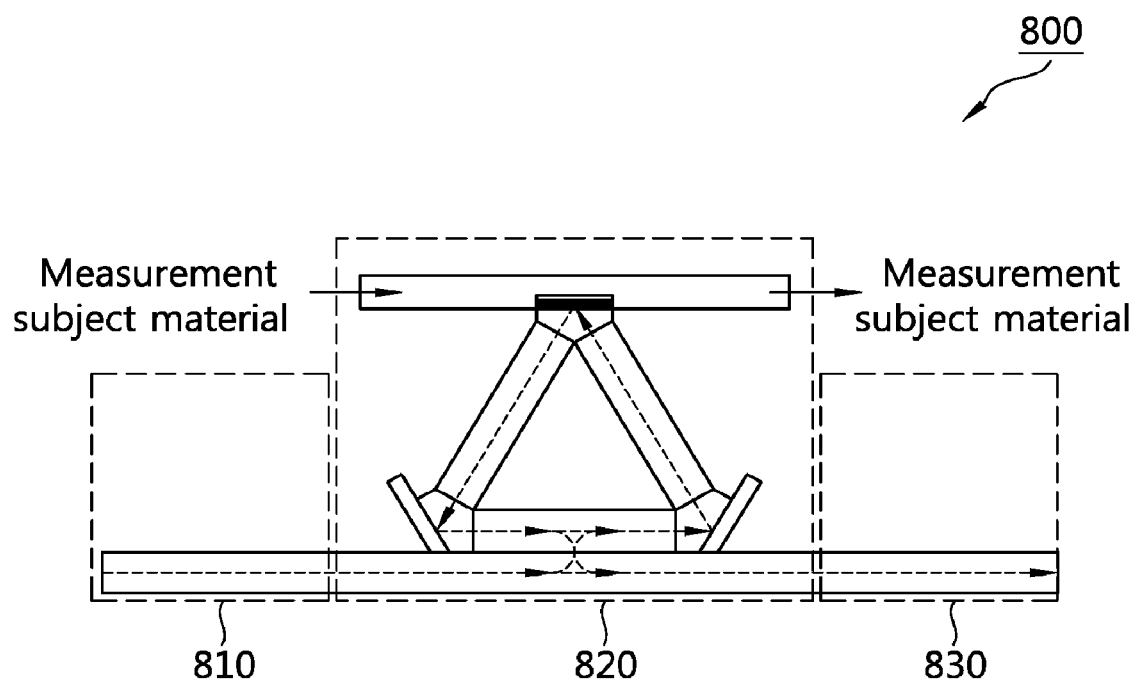
FIG. 8 illustrates the configuration of a micro-resonance sensor formed by combining a wavelength variable light source and a light detecting element to the micro-resonator sensor of FIG. 6 according to a fourth embodiment of the present invention.

FIG. 8 illustrates the configuration of a micro-resonance sensor formed by combining a wavelength variable light source and a light detecting element to the micro-resonator sensor of FIG. 6 according to a fourth embodiment of the present invention.

The micro-resonance sensor 800 as illustrated in FIG. 8 includes a light source unit 810, a resonating unit 820, and a detecting unit 830. The micro-resonance sensor 800 has a sensor module structure integrated as an on-chip on a wafer according to photonic integrated circuit (PIC) technique. In the micro-resonance sensor 800 using an evanescent wave of a total reflection mirror, the light source unit 810, the resonating unit 820, and the detecting unit 830 can be all fabricated in the form of waveguides, so the micro-resonance sensor 800 can be fabricated to be very small and integrated as an on-chip. Thus, the micro-resonance sensor 800 can be applicable to mobile equipments, and resonators of different sizes can be integrated to apply multiple wavelengths, to thus implement a multi-sensor. In addition, the main waveguide, the resonant waveguide, and the total reflection mirrors constituting the resonating unit 820 can be all fabricated with a similar material (e.g., a silica-based material), simplifying the process, and because they do not need to be in contact with a material (e.g., a metal layer) of completely different characteristics, such problems as complexity in the process otherwise caused as heterogeneous materials are attached, their adhesion, or the like, would not arise.

The micro-resonator sensor 600 according to the second embodiment of the present invention as shown in FIG. 6 is employed as the resonating unit 820 in FIG. 8, but the present invention is not limited thereto, and the micro-resonator sensor 500 according to the first embodiment of the present invention or the micro-resonator sensor 700 according to the third embodiment of the present invention can be also employed as the resonating unit 820 in a similar manner.

The preferred embodiments of the present invention have been described with reference to the accompanying drawings, and it will be apparent to those skilled in the art that various modifications and variations can be made in the present invention without departing from the scope of the invention. Thus, it is intended that any future modifications of the embodiments of the present invention will come within the scope of the appended claims and their equivalents.

The invention claimed is:

1. A micro-resonator sensor using an evanescent wave of a total reflection mirror, the sensor comprising:
   an input waveguide guiding inspection light incidented on one end section thereof to the other section;
   a total reflection mirror disposed at the other section of the input waveguide such that an incident angle made with the input waveguide is larger than a total reflection threshold angle at which the inspection light is totally reflected, and comprising a receptor provided on the other side from the side on which the inspection light is incidented and combined with a measurement-subject material; and
   an output waveguide disposed at a certain output angle relative to the total reflection mirror and outputting a reflection light whose intensity changes according to the measurement-subject material due to an interaction between the evanescent wave generated by the inspection light incidented to the total reflection mirror and the measurement-subject material.

2. The sensor of claim 1, wherein the incident angle is set such that energy in the form of an evanescent wave transferred to the side where a receptor of the total reflection mirror is provided is larger than a pre-set value.

3. The sensor of claim 1, wherein the incident angle and the output angle are the same.

4. The sensor of claim 1, further comprising:
   a light source unit that generates and emits the inspection light so as to be provided to the input waveguide; and
   a detecting unit that detects the intensity of outputted reflection light through the output waveguide to detect the characteristics of the measurement-subject material according to the intensity of the output reflection light.

5. The sensor of claim 4, wherein the light source unit, the input waveguide, the total reflection mirror, the output waveguide, and the detecting unit are integrated on a single wafer so as to be fabricated as a photonic integrated circuit.

6. A micro-resonance sensor using an evanescent wave of a total reflection mirror, the sensor comprising:
- a main waveguide comprising an input hole to which a optical signal is incidented and a output hole from which the optical signal is outputted and having a optical coupling region at which a portion of the optical signal incidented through the input hole is branched;
- a resonant waveguide comprising a optical coupling waveguide having a optical coupling region optically coupled with the optical coupling region of the main waveguide to receive the branch optical signal branched from the main waveguide, and a plurality of circumferential waveguides, the optical coupling waveguide and the circumferential waveguides of the resonance waveguide being disposed in a polygonal shape; and
- a plurality of optical path changing units disposed at vertex regions to which the optical coupling waveguide and the circumferential waveguides constituting the resonant waveguide are connected, and reflecting at least a portion of the branch optical signal inputted to the resonant waveguide so that the reflected optical signal can turn around within the resonant waveguide,
- wherein at least one of the optical path changing units disposed at the vertex regions to which the circumferential waveguides are connected is a total reflection mirror comprising a receptor provided on the other side from the side on which the branch optical signal is incidented and combined with a measurement-target material,
- the one circumferential waveguide, which makes the branch optical signal incident to the total reflection mirror, is disposed such that an incident angle relative to the total reflection mirror is larger than a total reflection threshold angle to make the branch optical signal incident on the total reflection mirror totally-reflected, the other circumferential waveguide, from which the branch optical signal totally reflected by the total reflection mirror is outputted, is disposed to make a certain output angle relative to the total reflection mirror, and
- resonance conditions of the resonant waveguide vary according to the measurement-subject material.

7. The sensor of claim 6, wherein the incident angle is set such that energy in the form of an evanescent wave transferred to the side where a receptor of the total reflection mirror is provided is larger than a pre-set value.

8. The sensor of claim 6, wherein the incident angle and the output angle are the same.

9. The sensor of claim 6, further comprising:
- an auxiliary waveguide disposed to be parallel to the main waveguide, wherein one end section of the auxiliary waveguide is optically coupled with the input hole of the main waveguide, and the other section of the auxiliary waveguide is optically coupled with the output hole of the main waveguide.

10. The sensor of claim 6, wherein the optical coupling waveguide and the main waveguide are integrally formed, and two of the optical path changing units are disposed at both end sections of the optical coupling region, respectively, wherein, among the both end sections of the optical coupling region, the optical path changing unit disposed at one end section of the optical coupling region adjacent to the output hole of the main waveguide is a first light branching element for branching the optical signal incidented through the input hole of the main waveguide to the output hole of the main waveguide and to the resonant waveguide, and the optical path changing unit disposed at the other section of the optical coupling region adjacent to the input hole of the main waveguide is a second light branching element for branching the branch optical signal which has turned around within the resonant waveguide to the main waveguide and to the resonant waveguide.

11. The sensor of claim 6, wherein the optical path changing units are total reflection mirrors installed at vertex regions to which the optical coupling waveguide and the circumferential waveguides constituting the resonant waveguide are connected, and totally reflecting the incident branch optical signal.

12. The sensor of claim 6, further comprising:
- a light source unit that generates and emits the optical signal and provides the optical signal to the input hole of the main waveguide; and
- a detecting unit that detects the intensity of outputted light through the output hole of the main waveguide to calculate a variation of resonance conditions of the resonant waveguide according to the measurement-subject material.

13. The sensor of claim 12, wherein the light source unit, main waveguide, the resonant waveguide, the optical path changing units, and the detecting unit are integrated on a single wafer so as to be fabricated as a photonic integrated circuit.

14. The sensor of claim 6, wherein optical coupling regions formed at the main waveguide and the resonant waveguide comprise a optical coupling element for coupling the optical signal incidented to the main waveguide to the resonant waveguide or the optical signal turning around within the resonant waveguide to the main waveguide, the optical coupling element being one of a vertical coupler, a directional coupler, and a multi-mode coupler.

* * * * *